(12) United States Patent
Wansing

(10) Patent No.: US 7,395,692 B2
(45) Date of Patent: Jul. 8, 2008

(54) PORTABLE GAS METER

(75) Inventor: Markus Wansing, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 15 days.

(21) Appl. No.: 11/463,754

(22) Filed: Aug. 10, 2006

(65) Prior Publication Data

US 2007/0089481 A1   Apr. 26, 2007

(30) Foreign Application Priority Data

Oct. 21, 2005   (DE) .................. 10 2005 050 914

(51) Int. Cl.
  *G01N 7/00*   (2006.01)
  *G01N 27/16*   (2006.01)
(52) U.S. Cl. .................. 73/23.2; 73/31.05; 422/94
(58) Field of Classification Search .............. 73/23.2, 73/23.31, 31.01, 31.05; 422/94
See application file for complete search history.

(56) References Cited

U.S. PATENT DOCUMENTS

| 4,517,161 | A | * | 5/1985 | Gravina et al. ................ 422/95 |
| 6,202,472 | B1 | | 3/2001 | Wezurek et al. |
| 6,728,643 | B2 | * | 4/2004 | Hackenberg et al. .......... 702/24 |
| 6,998,991 | B1 | * | 2/2006 | Goldstein et al. ........... 340/628 |
| 2006/0032745 | A1 | * | 2/2006 | Davies et al. ............... 204/431 |

FOREIGN PATENT DOCUMENTS

JP            7 35717       2/1995

* cited by examiner

*Primary Examiner*—Daniel S Larkin
(74) *Attorney, Agent, or Firm*—McGlew & Tuttle, P.C.

(57) ABSTRACT

A portable, preferably explosion-proof gas meter is improved in respect to shock loads and has a cylindrical measuring cell (5) and an evaluating circuit on a printed circuit board (6). The measuring cell (5) is connected to the printed circuit board (6) and is mounted in the housing in a shock-absorbing manner in the radial and longitudinal directions and is in gas flow connection with the environment through openings (40) in the housing.

18 Claims, 1 Drawing Sheet

PORTABLE GAS METER

CROSS REFERENCE TO RELATED APPLICATIONS

This application claims the benefit of priority under 35 U.S.C. § 119 of German Patent Application DE 10 2005 050 914.2 filed Oct. 21, 2005, the entire contents of which are incorporated herein by reference.

FIELD OF THE INVENTION

The present invention pertains to a gas meter with a housing with a cylindrical measuring cell and with an evaluating circuit on a printed circuit board.

BACKGROUND OF THE INVENTION

Such gas meters are so-called portable gas meters and are explosion-proof in a special design, and it is necessary at the same time that the explosion-proof quality be also preserved under shock loads. Especially explosion-proof, preferably cylindrical catalytic heat tone gas sensors are used as measuring cells to measure combustible gases in the environment of a measuring site because of their known measuring properties. Such a measuring cell appears, for example, from U.S. Pat. No. 6,202,472 B1. These measuring cells are measuring transducers for measuring the partial pressure of explosive gases in the ambient air. The ambient air to be monitored diffuses into the measuring cell through a sintered metal disk. The sintered metal disk prevents inflammation of the ambient air from the measuring cell. A detector element, a pellistor, which comprises a thin, coiled platinum wire, which is surrounded by a small ceramic bead with a catalytically active surface, especially one consisting of precious metals, is located in the measuring cell. The explosive gases are burned catalytically in a controlled manner at the heated detector element. The oxygen needed for the combustion is taken from the ambient air. The detector element is additionally heated by the heat of combustion, which is generated during the combustion and is characteristic of the burning gas or gases. This heating leads to a change in the resistance of the detector element, which is proportional to the concentration of the explosive gases. Besides the catalytically active detector element, a likewise heated, inactive pellistor, the compensator element, is located in the measuring cell. Both elements are part of a bridge circuit, especially a Wheatstone bridge. Environmental effects, such as temperature, humidity or thermal conduction of the ambient air to be monitored, act on both elements to an equal extent, as a result of which these effects on the measured signal are compensated nearly completely. Catalytic heat tone gas sensors have been used in large numbers for measurement and early warning for many years where combustible gases or vapors may form explosive mixtures together with air. Portable gas meters and especially explosion-proof gas meters are exposed to high mechanical loads, and to preserve the operating reliability, they should be designed such that they are fall-proof and shock-proof. Prior-art solutions heretofore are, for example, a rubber jacketing of the meter, which has the drawback that a thick layer of damping material must be applied for a sufficient mechanical damping, so that the gas meter becomes bulky and heavy.

SUMMARY OF THE INVENTION

Thus, the object of the present invention is to provide improved shock absorption for a gas meter and especially for the measuring cell in the meter, so that the measuring properties of the measuring cell are not compromised, on the one hand, and the solution is efficient for the gas meter, on the other hand.

According to the invention, a gas meter is provided with a housing, a measuring cell and an evaluating circuit on a printed circuit board. The measuring cell is connected to the printed circuit board and is in gas flow connection with the environment via openings in the housing. The measuring cell is mounted in the housing in a shock-absorbing manner in the direction from and to the openings and in the direction at right angles thereto.

The measuring cell may be mounted by holding elements. These may be located at a spaced location in the longitudinal direction of the measuring cell and are connected to the housing. These may consist of an elastomer.

Additional, shock-absorbing, especially ring-shaped or disk-shaped intermediate elements may be arranged between the measuring cell and the holding elements in the longitudinal direction of the measuring cell. The intermediate elements may be made of a foamed polymer or a foam rubber, preferably of a closed-cell foam rubber.

The holding elements may be inherent or integral parts of the housing or may be manufactured by injection molding and be connected to the housing.

The housing may comprise a plurality of assembled housing parts. The housing parts may consist of plastic components having different hardnesses.

The measuring cell may be a catalytic heat tone gas sensor for the measurement of combustible gases.

One or more electrochemical gas sensors for the measurement of different individual gases, which are likewise connected to the evaluating circuit on the printed circuit board may be additionally installed.

The measuring cell may be arranged vertically through an opening in the printed circuit board and may be connected to same in a mobile manner.

The measuring cell may be covered toward the environment by a semipermeable membrane, so that the gas meter is water-proof and permeable to gases on the measuring side of the measuring cell toward the environment through the openings.

The gas meter may be equipped with signal-generating means for visual and/or audio displays. The gas meter is advantageously explosion-proof.

The measuring cell may be mechanically uncoupled from the printed circuit board by means of a elastic, flexible connection element. The measuring cell may be electrically connected to the printed circuit board.

The measuring cell may advantageously be designed in the form of a cylinder and mounted in the housing in a shock-absorbing manner in the direction of its longitudinal axis from and to the openings as well as in circumferentially radial directions at right angles to the longitudinal axis.

The necessary shock absorption is achieved by the intermediate elements between the measuring cell and the holding elements in the longitudinal direction of the measuring cell. The intermediate elements are preferably made of an elastomer, especially preferably a foamed elastomer.

As a result, it is especially advantageous that only the mass of the measuring cell, which is substantially lower than that of the gas meter, is damped, e.g., 17 g in a concrete application compared to 200 g to 300 g for the gas meter, depending on the equipment.

An exemplary embodiment of a gas meter will be explained below on the basis of the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
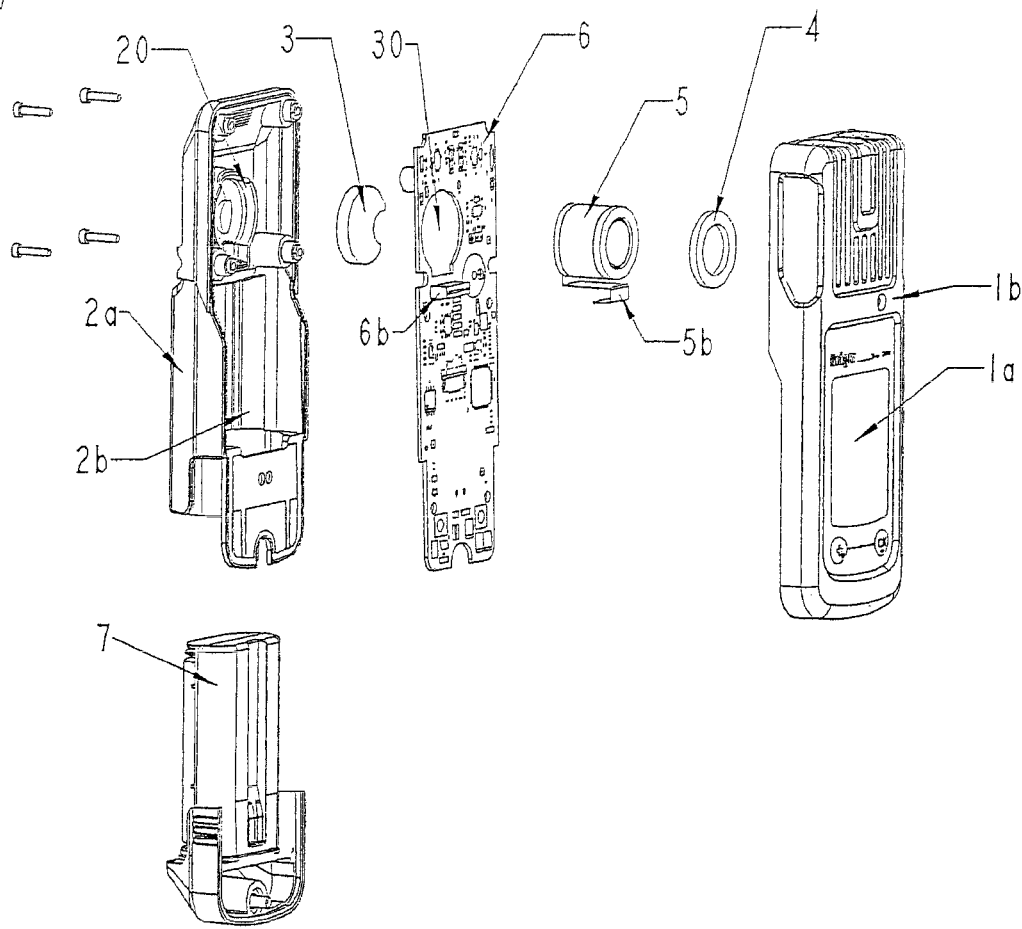
FIG. 1 is an exploded view of a gas meter with the essential components.
Figure 2:
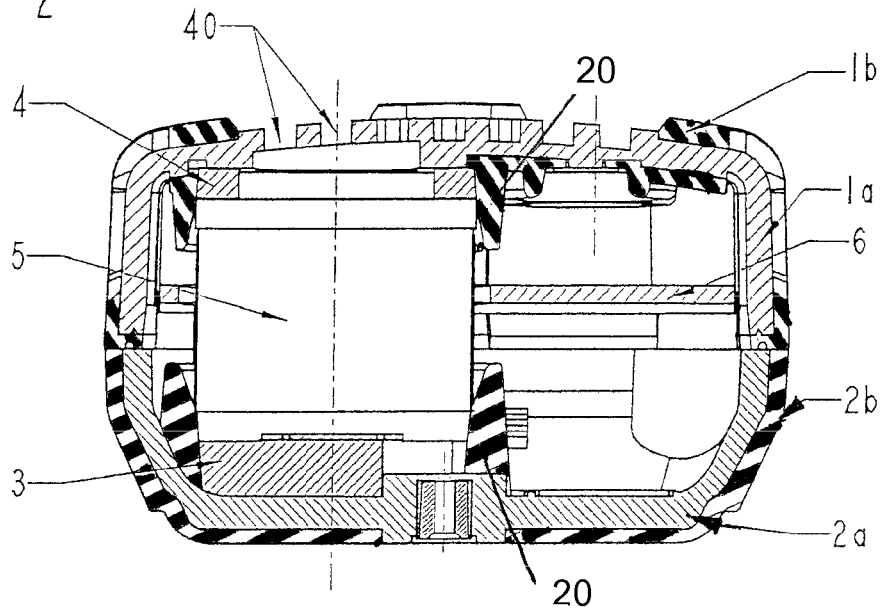
FIG. 2 is a sectional view through the assembled gas meter according to FIG. 1 at right angles to the longitudinal axis of the measuring cell.

Referring to the drawings in particular, a portable gas meter in FIG. 1 has a housing, a measuring cell 5 and an evaluating circuit on a printed circuit board 6. The measuring cell 5 is connected to the evaluating circuit on the printed circuit board 6 and is in gas flow connection with the environment via openings in the housing. The measuring cell 5 is mounted in the housing in a shock-absorbing manner in the direction from and to the openings and in the direction at right angles thereto. The housing is composed of a plurality of housing parts housing 1a, 1b, 2a, 2b. The front shell comprises a hard component 1a, made, for example, of a polycarbonate, and a soft component 1b, made, for example, of a thermoplastic elastomer. The rear shell likewise comprises a hard component 2a and a soft component 2b. On the two inner sides of the housing, the soft component 1b, 2b forms a ring-shaped holding element 20 each for receiving the measuring cell 5, which is especially a catalytic heat tone gas sensor. As a result, the measuring cell 5 can vibrate in a damped manner in the radial direction, i.e., at right angles to its longitudinal axis. The mount is made so strong that the measuring cell 5 can move into the end position during the maximally occurring shock load. This is at a distance of 1 mm to 2 mm in each direction from the original position. Damping intermediate elements 3, 4 made, for example, of a foamed polymer or a foam rubber are arranged in front of and behind the measuring cell 5. These permit a damped motion in the direction of the longitudinal axis of the measuring cell 5. An opening 30, which is so large that a possible motion of the measuring cell 5 is not hindered during a shock, is provided in the printed circuit board 6.

The measuring cell 5 is connected to the plug 6b with a mobile, flexible connection element 5b. There is a gas flow connection with the environment via the openings 40 in the housing. The component 7 is an optional housing part, which is used as an electric supply unit. The actual dimensions of the portable gas meter in the embodiment shown are 130 mm×46 mm×32 mm for the gas meter and 20 mm×16 mm for the cylindrical measuring cell 5. A plurality of electrochemical gas sensors for the specific measurement of certain gases, especially $CO$, $O_2$, $H_2S$, are additionally provided for a multiple gas meter.

The gas meter is preferably designed as an explosion-proof meter due to corresponding sealing of the assembled housing and/or due to the explosion-proof design of the electric components.

While specific embodiments of the invention have been shown and described in detail to illustrate the application of the principles of the invention, it will be understood that the invention may be embodied otherwise without departing from such principles.

What is claimed is:

1. A gas meter comprising:
   a housing;
   a measuring cell; and
   an evaluating circuit on a printed circuit board, said measuring cell being connected to said printed circuit board and being in gas flow connection with the environment via openings in the housing, said measuring cell being mounted in the housing in a shock-absorbing manner in the direction from and to said openings and in the direction at right angles thereto.

2. A gas meter in accordance with claim 1, wherein said measuring cell is mounted by holding elements located at a spaced location in a longitudinal direction of said measuring cell, said holding elements comprising an elastomer forming a part of said housing.

3. A gas meter in accordance with claim 2, further comprising additional, shock-absorbing, ring-shaped or disk-shaped intermediate elements arranged between said measuring cell and said holding elements in the longitudinal direction of said measuring cell.

4. A gas meter in accordance with claim 3, wherein said intermediate elements comprise a foamed polymer or a closed-cell foam rubber.

5. A gas meter in accordance with claim 2, wherein said holding elements are integral parts of said housing or are manufactured by injection molding and are connected to said housing.

6. A gas meter in accordance with claim 1, wherein said housing comprises a plurality of assembled housing parts, wherein said housing parts are formed of plastic components having different hardnesses.

7. A gas meter in accordance with claim 1, wherein said measuring cell is a catalytic heat tone gas sensor for the measurement of combustible gases.

8. A gas meter in accordance with claim 1, further comprising an electrochemical gas sensor for the measurement of different individual gases, said electrochemical gas sensor being connected to the evaluating circuit on said printed circuit board.

9. A gas meter in accordance with claim 1, wherein said measuring cell is arranged vertically through an opening in said printed circuit board and is connected to said printed circuit board in a mobile manner.

10. A gas meter in accordance with claim 1, wherein the gas meter is explosion-proof.

11. A gas meter in accordance with claim 1, further comprising an elastic, flexible connection element wherein said measuring cell is mechanically uncoupled from said printed circuit board by said elastic, flexible connection element and is electrically connected to said printed circuit board.

12. A gas meter in accordance with claim 1, wherein said measuring cell comprises a cylinder mounted in said housing in a shock-absorbing manner in the direction of a longitudinal axis of said cylinder and from and to said openings as well as in circumferentially radial directions at right angles to the longitudinal axis.

13. A gas meter comprising:
   a housing with an opening;
   a measuring cell;
   an evaluating circuit on a printed circuit board, said measuring cell being connected to said printed circuit board and being disposed in said housing with said printed circuit board in gas flow connection with the environment via said opening; and shock absorbing mounting elements disposed between said measuring cell and a part of said housing on at least two sides of said measuring cell for absorbing shock in the direction from and to said openings and in the direction at right angles thereto.

14. A gas meter in accordance with claim 13, wherein said shock absorbing mounting elements comprise holding elements located at a spaced location in a longitudinal direction of said measuring cell, said holding elements comprising an elastomer forming a part of said housing.

15. A gas meter in accordance with claim 14, further comprising additional shock-absorbing elements arranged between said measuring cell and said holding elements in the longitudinal direction of said measuring cell.

16. A gas meter in accordance with claim 15, wherein said intermediate elements comprise a foamed polymer or a closed-cell foam rubber.

17. A gas meter in accordance with claim 13, wherein said housing comprises a plurality of assembled housing parts, wherein said housing parts are formed of plastic components having different hardnesses and include said part of said housing and said absorbing mounting elements, said part of said housing being harder than said absorbing mounting elements.

18. A gas meter in accordance with claim 13, wherein said measuring cell is a catalytic heat tone gas sensor for the measurement of combustible gases.

* * * * *